US00PP29559P3

(12) United States Plant Patent
Hansen

(10) Patent No.: US PP29,559 P3
(45) Date of Patent: Jul. 31, 2018

(54) ***HOSTA* PLANT NAMED 'SCHOOL MOUSE'**

(50) Latin Name: ***Hosta* hybrid (Tratt.)**
Varietal Denomination: School Mouse

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/530,299

(22) Filed: Dec. 20, 2016

(65) Prior Publication Data

US 2018/0177097 P1 Jun. 21, 2018

(51) Int. Cl.
*A01H 5/12* (2018.01)
*A01H 5/02* (2018.01)

(52) U.S. Cl.
USPC ..... Plt./353
CPC ..... *A01H 5/02* (2013.01); *A01H 5/12* (2013.01)

(58) Field of Classification Search
USPC ..... Plt./353
CPC ..... A01H 5/12; A01H 5/02; A01H 5/0272; A01H 5/00
See application file for complete search history.

(56) References Cited

PUBLICATIONS

Walters Gardens, Inc. Summer 2016-Spring 2017 catalog, retrieved on Jan. 18, 2018, retrieved from the Internet at https://cld.bz/users/user-9rLuGlj/Walters-Gardens-2017-catalog/204, pp. 1, 6-8, 137, 202-203. (Year: 2016).*

* cited by examiner

*Primary Examiner* — June Hwu

(57) ABSTRACT

A new and distinct *Hosta* plant named 'School Mouse' with coarsely-sinuate cordate leaf blades having variegation of creamy yellow margins and dark green center and feathering intermediate colors. The plant habit is short, compact and rounded with flowering just above foliage, and the leaves and scapes are thick substance and stiff, flowering just above the foliage with medium lavender flowers with strongly veined deep lavender and white insides.

1 Drawing Sheet

Botanical classification: *Hosta* hybrid (Tratt.).
Variety denomination: 'School Mouse'.

BACKGROUND AND ORIGIN OF THE PLANT

The present invention relates to a new and distinct *hosta* plant, *Hosta* 'School Mouse' hereinafter also referred to as the new plant or just the cultivar name, 'School Mouse'. *Hosta* 'School Mouse' was discovered by the inventor as a non-induced, naturally-occurring, whole-plant mutation in a batch of tissue cultured *Hosta* 'Church Mouse' (not patented) at a nursery greenhouse in Zeeland, Mich., USA during the summer of 2012. The new plant has been asexually propagated by division at the same nursery in Zeeland, Mich. USA since 2014 and also by careful shoot tip plant tissue culture with the resultant asexually propagated plants having retained all the same traits as the original plant. 'School Mouse' is stable and reproduces true to type in successive generations of asexual reproduction.

*Hosta* 'School Mouse' has not been made publically available or sold anywhere in the world prior to the filing of this application except for disclosures by the inventor, or one who obtained the material either directly or indirectly from the inventor, and any such disclosure has not been made more than one year prior to the application of this invention.

There are over 5,600 registered *hostas* with The American *Hosta* Society, which is the International Cultivar Registration Authority for the genus *Hosta*. *Hosta* 'School Mouse' is a sport from 'Church Mouse' (not patented) which is one of many sports with similar habit all from *Hosta* 'Blue Mouse Ears' (not patented). The most similar *hosta* cultivars known to the applicant are *Hosta* 'Church Mouse' and 'Mini Skirt' U.S. Plant Pat. No. 26,743. 'Church Mouse' has a similar leaf undulation but differs in that the new plant has a margin with a lighter yellow coloring rather than the margin of 'Church Mouse' with a margin that differs only slightly from the blue-green center with green leaf margin. *Hosta* 'Mini Skirt' has a creamy yellow to creamy white margin, but has less pronounced leaf undulations. Another cultivar, 'Ruffled Mouse Ears' (not patented), has similar sport history, both originally arising from 'Blue Mouse Ears'. 'Ruffled Mouse Ears' has a similar coarse wave to the leaves but is not variegated. *Hosta* 'Mighty Mouse' (not patented) is a sport of 'Blue Mouse Ears' with foliage having a creamy yellow to creamy white margin and green center but also has a flatter leaf.

Other *Hosta* cultivars have short habit and variegation of a similar nature, or other individual traits similar to 'School Mouse' but the new plant differs from the above cultivars and all other *hostas* known to the applicant, by the combination of the following traits.

1. Cordate, coarsely sinuate leaves.
2. Leaves with creamy yellow margins and dark green center and feathering intermediate colors.
3. Stiff scapes and leaves with thick substance.
4. Short, compact, rounded habit with dense flowering just above foliage.

5. Flowers of medium lavender and inside strongly veined with deep lavender and white.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings shows a two-year-old plant in a container in mid-season grown in a shaded greenhouse at a nursery in Zeeland, Mich. with supplement fertilizer and water as needed.

FIG. 1 shows the foliage and habit of the plant.

DETAILED BOTANICAL DESCRIPTION

The following descriptions and color references are based on the 2001 edition of The Royal Horticultural Society Colour Chart except where common dictionary terms are used. The new plant, *Hosta* 'School Mouse', has not been observed under all possible environments. The phenotype may vary slightly with different environmental conditions, such as temperature, light, fertility, moisture and maturity levels, but without any change in the genotype. The following observations and size descriptions are of a potted two-year-old plant in a shaded greenhouse in Zeeland, Mich. with supplemental water and fertilizer.

Botanical classification: *Hosta* hybrid;

Parentage: Whole-plant mutation of *Hosta* 'Church Mouse' (not patented);

Propagation: Garden division and sterile plant tissue culture;

Time to initiate roots from tissue culture: About two to three weeks;

Growth rate: Moderate;

Crop time: About 12 weeks to finish during the summer in a one-liter container from rooted tissue culture plantlet;

Rooting habit: Fleshy, lightly branching;

Plant shape and habit: Hardy herbaceous perennial with basal rosette of leaves emerging from rhizomes producing a short symmetrical mound of broadly-horizontal sinuate leaves;

Plant size: Foliage height 9.0 to 12.0 cm above soil line to the top of the leaves and about 24.0 to 28.0 cm wide at the widest point just above soil line;

Foliage description: Entire, glabrous, slightly glaucous above and more glaucous below, cordate, broadly acute leaf apex with cordate base; coarsely sinuate to slightly tortuous;

Leaf blade: To about 6.7 cm long and about 6.0 cm wide; average about 5.4 cm long and 5.3 cm wide; dark green center and light yellow margin that varies between leaves and locations on leaves from 6.0 mm to 18.0 mm wide; surface smooth without dimpling, bulging or blistering;

Leaf blade color: Early season still expanding adaxial center color nearest RHS 137A; early season adaxial margin nearest RHS 144A; early season abaxial center nearest RHS 144A; early season abaxial margin between RHS N138B and RHS N138C; mid-season and later summer adaxial center nearest RHS 143A; mid-season and later adaxial margins nearest RHS N144A; mid-season and later abaxial center nearest RHS 144B; mid-season and later abaxial margins nearest RHS N144A to RHS 151D depending on light exposure; small irregular segments of intermediate colors where adaxial margin and center unevenly and irregularly fold over each other comprising nearest RHS 143B, nearest RHS 144B and nearest RHS 151A; irregular intermediate abaxial comprising colors of nearest RHS 143B, nearest RHS 144C and nearest RHS 151C;

Petiole: Entire; glabrous both surfaces; concavo-convex; mostly straight from base of plant to leaf base with little bending or arching, stiff; to 6.5 cm long and 1.4 cm wide at base, average 5.2 cm long and 10.0 mm wide at base;

Petiole color: Early season still expanding adaxial center color nearest RHS 144B; early season adaxial margin between RHS 144A and RHS 144B; early season abaxial center nearest RHS 144B; early season abaxial margin nearest RHS 144A; mid-season and later summer adaxial center nearest RHS 137A; mid-season and later adaxial margins between RHS 145A and RHS 146D; mid-season and later abaxial center nearest RHS N138C; mid-season and later abaxial margins nearest RHS 147C;

Veins: Parallel, raised on abaxial side, normally 8 pairs on either side of midrib;

Veins color: On adaxial margin of expanding and mature leaves nearest RHS N144D, all other veins same color as the surrounding tissue;

Flower description:

Inflorescence: Average 14.0 cm tall, and flowering in the terminal 7.0 cm to a width of about 4.2 cm wide;

Buds one day prior to opening: Globose with rounded apex and terete base; about 1.2 cm in diameter with base narrowing at about mid-length to about 3.0 mam diameter; about 2.4 cm long;

Bud color: Between RHS 85B and RHS 91B with stripes of nearest RHS 85D;

Flowers: Perfect; single; perianth shape funnelform; held nearly horizontal to slightly drooping; corolla tube about 2.2 cm wide and about 2.5 cm long, (distal flowers smaller), fused in basal about 1.8 cm with basal about 1.2 cm forming a tube about 3.5 mm diameter; persists for a normal period, usually one day on plant or as cut flower; scapes remain effective with flowers from late June to mid-July with 14 to 18 flowers per scape; no detectable fragrance;

Tepal: Two sets of three, glabrous, entire; fused at base; clavate with broadly acute apex; each approximately 2.5 cm long and 1.1 cm wide;

Tepal color: Inner set with thin transparent margin about 1.0 mm wide; both tepal sets with adaxial base of white, lighter than RHS 155D, adaxial longitudinal middle nearest 76A with veins of between RHS 77A and RHS 77B and distal one-third between RHS 76A and RHS 76B; abaxial basal tube of both tepal sets nearest RHS 76D with lighter than RHS N77D at point of attachment; abaxial inner tepal set longitudinal middle and distally nearest 76B with abaxial outer tepal set longitudinal middle and distally nearest RHS 76C with about nine veins of nearest RHS 76B; abaxial corolla tube nearest very pale purple;

Gynoecium: Single;

*Style*.—Single, approximately 2.6 cm long, 1.5 mm diameter, curved upward slightly in distal 1.0 cm; color distally lighter than RHS 155D, base nearest RHS 146B.

*Stigma*.—Globose, about 2 mm in diameter, nearest RHS 145C.

Androecium:

*Filaments*.—Six, approximately 2.2 cm long and 1.0 mm in diameter; curved upward to nearly 90 degrees in the apical 1.0 cm; color distal one-half white, lighter than RHS 155D, basal one-half between RHS 145A and RHS 145B.

*Anthers*.—Elliptic; dorsifixed, dehiscent longitudinally; about 3.0 mm long, 2.0 mm wide; color nearest RHS 200D with undertone of nearest RHS 22D prior to dehiscing and after dehiscing between RHS N92A and RHS 202A.

*Pollen*.—Elliptic, abundant; less than 0.1 mm long, color nearest to RHS 17A.

Peduncle: Usually one per mature division; glaucous, glabrous; stiff; nearly vertical; 12 to 16 cm long, flowering in distal 7.0 cm; 5 mm in diameter at base;

Peduncle color: Nearest RHS 137B;

Pedicel: Short, glabrous; approximately 5.0 mm long, 2.0 mm diameter; nearest RHS 146D with tinting of nearest RHS N77D where exposed to more light;

Scape bracts: Each flower normally subtended by a single bract, decreasing in size distally with one or two below first flowers; bracts subtending flowers protruding to nearly perpendicular to scape; concavo-convex supporting flower bud; first bract subtending flower about 12.0 mm long and 8.0 mm wide;

Scape bract color: Adaxial nearest RHS 146B distally, nearest RHS 146D base and margin between RHS 148D and RHS 145B; abaxial margin blend between RHS 148D and RHS 145D and center nearest RHS 137B;

Fruit: Not yet observed;

Seed: Not yet observed; infrequent or sterile under present growing conditions; believed to be sterile or recalcitrant;

Disease resistance: The new plant has not shown any resistance to pests and diseases common to *hostas*. The plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3 through 9, and other disease resistance is typical of that of other *hostas*.

It is claimed:

1. A new and distinct ornamental plant cultivar named *Hosta* 'School Mouse' as herein described and illustrated.

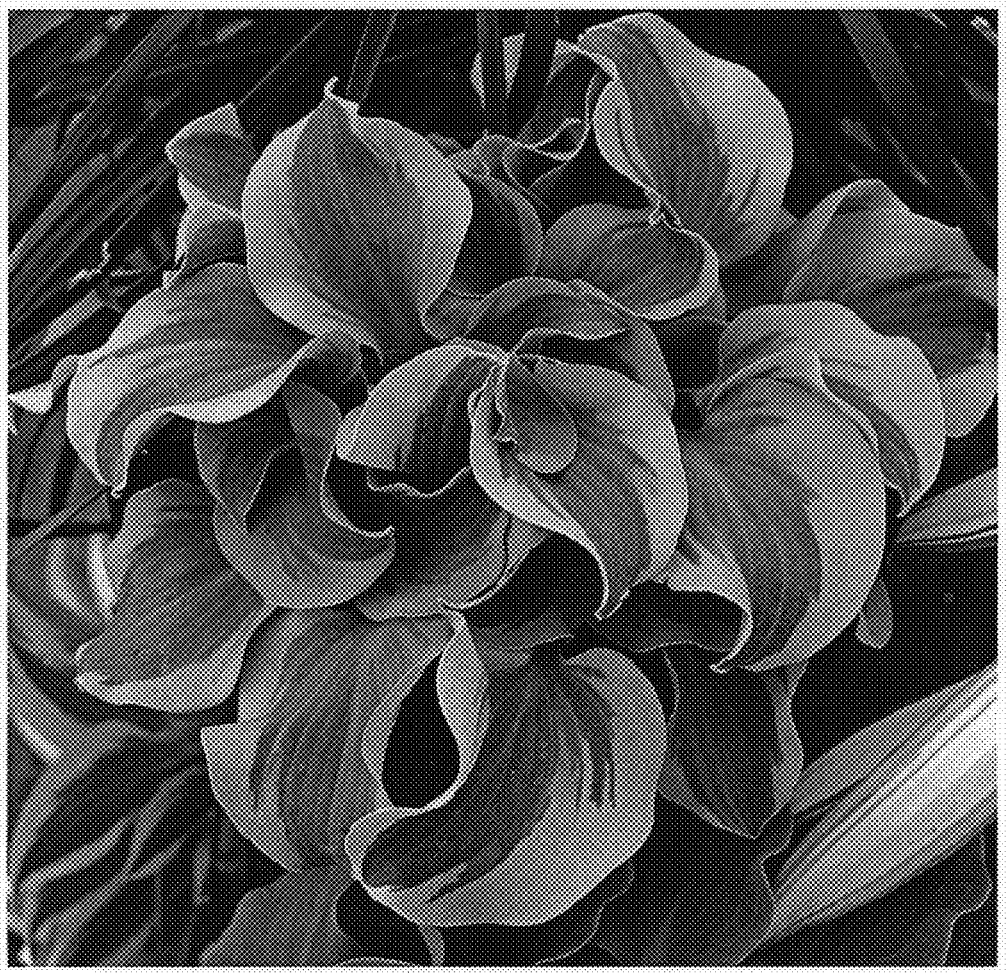

* * * * *